United States Patent [19]

Straw et al.

[11] Patent Number: 4,695,451

[45] Date of Patent: Sep. 22, 1987

[54] AEROSOL ANTIPERSPIRANT COMPOSITION

[75] Inventors: Alan Straw, Macclesfield; Stewart Shields, Salford, both of England

[73] Assignee: Colgate-Palmolive Company, New York, N.Y.

[21] Appl. No.: 335,991

[22] Filed: Dec. 30, 1981

[51] Int. Cl.$^4$ .......... A61K 7/32; A61K 7/34; A61K 7/36; A61K 7/38

[52] U.S. Cl. .......... 424/47; 424/65; 424/66; 424/67; 424/68

[58] Field of Search .......... 424/47, 68

[56] References Cited

U.S. PATENT DOCUMENTS

| 3,395,028 | 7/1968 | Mackles | 106/8 |
| 3,509,523 | 4/1970 | Babbin | 424/47 |

FOREIGN PATENT DOCUMENTS

| 1076030 | 4/1980 | Canada | 424/47 |
| 1092030 | 12/1980 | Canada | 424/47 |
| 2301829 | 7/1973 | Fed. Rep. of Germany | 424/47 |
| 779899 | 8/1972 | France | 424/47 |
| 1487812 | 10/1977 | United Kingdom | 424/68 |

*Primary Examiner*—Dale R. Ore
*Attorney, Agent, or Firm*—Richard N. Miller; Murray M. Grill; Herbert S. Sylvester

[57] ABSTRACT

An aerosol antiperspirant composition in the form of a substantially stable water-in-oil emulsion is disclosed which consists of 25% to 50% by weight of a liquefied, normally gaseous propellant and 50% to 75% of a base consisting essentially of, by weight, 4 to 20% of at least one water-soluble, astringent salt having antiperspirant efficacy; 0.5 to 5% of a water-in-oil emulsifier; 10% to 25% of a propellant-soluble emollient-stabilizer agent consisting of a water-insoluble, organic, liquid emollient and a water-insoluble organic liquid having a boiling point in the range of 35° C. to 155° C., the weight ratio of emollient to organic liquid being in the range of 0.8:1 to 3:1, and 55% to 78% of water. In preferred compositions, $C_3$–$C_4$ hydrocarbon propellants are employed.

9 Claims, No Drawings

AEROSOL ANTIPERSPIRANT COMPOSITION

BACKGROUND OF THE INVENTION

This invention relates to an improved aerosol antiperspirant composition in the form of a substantially stable water-in-oil emulsion. More particularly, such improved antiperspirant compositions consist of a propellant and a base consisting essentially of a mixture of water and a water-soluble antiperspirant salt dispersed in a continuous phase containing an emollient-stabilizer agent and a water-in-oil emulsifier.

Antiperspirant compositions are well known and in wide use. Generally, such compositions employ compounds or complexes of aluminum as the active antiperspirant agent, and these compositions have been available in the form of a powder, a lotion, a cream, a liquid, a liquid spray and an aerosol. In recent years, the aerosol form has been very widely used, most commonly as anhydrous dispersions of particles of antiperspirant agents in an organic solvent-propellant liquid mixture. Solutions of antiperspirant agents in alcohol or alcohol/water propelled by a propellant produced wet sprays and were subject to severe container corrosion.

While each type of aerosol antiperspirant had its own particular problems and shortcomings, each type of aerosol utilized a chlorofluorohydrocarbon propellant because the resultant product was nonflammable. In fact, the flammable character of ethanol and hydrocarbon propellants tended to limit the use of these materials in aerosol antiperspirants. However, in view of the environmentalists' recent concern with the possible depletion of the ozone layer in the atmosphere which allegedly is related to the use of chlorofluorohydrocarbon propellants, a need exists to develop aerosol antiperspirants which do not employ such chlorinated propellants.

In order to fulfill the foregoing need, research again has been directed toward formulation of non-flammable aerosol antiperspirant compositions which preferably employ hydrocarbon propellant. One proposed product is the water-in-oil emulsion antiperspirant composition described in Canadian No. 1,076,030 wherein an aqueous solution of antiperspirant agent is dispersed in a liquid mixture of hydrocarbon propellant and an emollient oil. However, such compositions tend to lead an oily residue on the skin.

SUMMARY OF THE INVENTION

The improved aerosol antiperspirant composition appear to be an improvement over the prior art antiperspirant compositions of the water-in-oil type because they leave a deposit on the skin which is less oily. Additionally, the improved compositions exhibit good stability based upon the presence of a mixture of propellant-soluble, water-insoluble, organic liquids as an emollient stabilizer agent. Finally, the method of manufacture facilitates preparation of stable emulsions containing maximum amounts of water which are less expensive and easy to perfume.

Broadly, the improved aerosol antiperspirant compositions in the form of a substantially stable water-in-oil emulsion consist of 25% to 50% by weight of a liquified, normally gaseous propellant and 50% to 75% to a base consisting essentially of by weight:

A. 4% to 20% of at least one water-soluble, astringent salt having antiperspirant efficacy;
B. 0.5% to 5% of a water-in-oil emulsifier;
C. 10% to 25% of a propellant-soluble emollient-stabilizer agent consisting of (1) a water-insoluble, organic, liquid emollient and (2) a water-insoluble, organic liquid having a boiling point in the range of 35° C. to 155° C., the weight ratio of (1) to (2) being in the range of 0.8:1 to 3:1; and
D. 55% to 78% of water, said base being in the form of a substantially stable water-in-oil emulsion. Such compositions are stable upon aging at a temperature in the range of 4° C. to 43° C. and are non-flammable when hydrocarbon propellant is employed.

Preferred compositions consist of 30% to 40% by weight of a $C_3$–$C_4$ hydrocarbon propellant and 60% to 70% by weight of a base consisting essentially of by weight:

A. 10% to 16% of basic aluminum chloride;
B. 0.75% to 4% of sorbitan sesquioleate;
C. 12% to 18% of a mixture of (1) an isopropyl ester of a $C_{12}$–$C_{16}$ alkanoic acid and (2) a liquid hydrocarbon having a boiling point in the range of 97° C. to 104° C. with the weight ratio of (1) to (2) being in the range of 2:1 to 1:1; and
D. 65% to 75% of water.

Also within the scope of the claimed invention is the process of making an article of manufacture which consists of a container containing a water-in-oil emulsion which comprises the steps of:

A. Forming a liquid mixture at a temperature of from 10° C. to 40° C. of 12 to 18 parts by weight of an isopropyl ester of a $C_{12}$–$C_{18}$ alkanoic acid and a liquid hydrocarbon having a boiling point in the range of 97° C. to 104° C. with the weight ratio of said ester to said hydrocarbon being from 2:1 to 1:1;
B. Dissolving an oil-in-water emulsifier in the liquid mixture of Step A with agitation;
C. Adding 8 to 22 parts by weight of water to the mixture of Step B with vigorous agitation to form a water-in-oil emulsion;
D. Adding from 50 to 80 parts by weight of an aqueous solution of aluminum chlorohydroxide to the water-in-oil emulsion of Step C with strong agitation;
E. Filling 60 to 70 parts by weight of the water-in-oil emulsion of Step D into an aerosol container and closing said container with a vapor tap valve; and
F. Adding 30 to 40 parts by weight of a $C_3$–$C_4$ hydrocarbon propellant under pressure to said aerosol container through the valve thereof and agitating the contents whereby a substantially stable aerosol antiperspirant composition is formed.

Such process facilitates preparation of stable emulsions since the emulsion is achieved before being added to the container wherein continuous phase of the emulsion simply is diluted upon addition of the propellant.

As indicated heretofore, the stability of the emulsion is achieved by proper selection and proportioning of the ingredients comprising the emollient-stabilizer agent. Emulsion stability is very important from the standpoint of avoiding the corrosion of metal containers which would result if a separate water phase were present or if water were present in the continuous phase of the emulsion. For example, use of other related emollients, such as either diisopropyl adipate or cetyl alcohol in place of equal parts of isopropyl myristate and an octane fraction, resulted in an unstable product. Additionally, such improved stability is surprising since the proportion of the dispersed water phase has been increased. In fact, as the dispersed water phase usually exceeds about 80% by weight of the base prior to dilution with liquid propellant, it would be expected that an oil-in-water emulsion rather than a water-in-oil emulsion would result. Additionally, the proportions of essential components in the final product do not result in reversion of the water-in-oil emulsion when it is sprayed from the container.

DETAILED DESCRIPTION OF INVENTION

The aerosol antiperspirant compositions of this invention in the form of water-in-oil emulsions consist of a liquefied, normally gaseous propellant and a base which consists essentially of specific proportions of four components, namely, a water-soluble, astringent salt having antiperspirant efficacy; a water-in-oil emulsifier; an oil-soluble, water-insoluble emollient-stabilizer agent and water. Optional components include a perfume and a bulking agent.

The propellants employed in the inventive antiperspirant compositions are well known in the art. In general, any liquefied, normally gaseous, organic material which is non-toxic and non-reactive with the other components of the composition can be used. Suitable propellants include the $C_3$–$C_4$ aliphatic hydrocarbons and the chlorofluoro hydrocarbons containing 1–4 carbon atoms. Examples of the aliphatic hydrocarbons are liquefied propane, n-butane and isobutane. Examples of the chlorofluoro hydrocarbons are dichlorodifluoromethane, monochlorodifluoromethane, difluoromonochloroethane, trichlorotrifluoroethane, monofluorodichloromethane, monofluorodichloroethane, pentafluoromonochloroethane; cyclic hexafluorodichlorobutane, octafluoropropane, and cyclic octafluorobutane; and mixtures thereof. For enviromental reasons, the preferred propellants are the $C_3$–$C_4$ hydrocarbons, with mixtures of isobutane and propane being particularly preferred.

The proportion of propellant in the inventive compositions depends upon the particular propellant(s) selected. Typically, the propellant which is selected should provide a vapor pressure in the range of 15 p.s.i.g. to 100 p.s.i.g. at 23° C. which is effective to disperse the contents of the container. Usually, the proportion of propellant in the aerosol composition will be from about 25% to 50%, preferably 30% to 40%, by weight.

Like the propellant component, the active antiperspirant component used in the inventive aerosol composition also is well known to those skilled in the art. Generally, any water-soluble astringent salt having antiperspirant efficacy may be used, provided that it is insoluble in the propellant. The usual astringents are water-soluble salts, including hydrates, or complexes of aluminum, zinc or zirconium. Examples of suitable salts are zirconium tetrachloride, zirconium oxychloride, zirconyl hydroxychloride, zirconium sulfate, zinc hydroxychloride, zinc hydroxybromide, zinc sulfate, aluminum basic chloride, aluminum chloride, aluminum bromide, aluminum sulfate, aluminum oxychloride, aluminum oxysulfate, aluminum chloride hexyhydrate, alumiminum lactate, aluminum sulfamate and aluminum phenolsulfonate. The preferred antiperspirant ingredients are the "aluminum basic chlorides" having the empirical formula $Al_2(OH)_{6-x}Cl_x$ wherein x is a postive number from 1 to 5 and the organic complexes, e.g., polyol and glycine complexes, of said basic chlorides.

In the aerosol, water-in-oil emulsion, antiperspirant compositions of this invention, the antiperspirant component is present in the dispersed phase of the base. The proportion of antiperspirant component based upon the weight of the base is usually from 4% to 20%, preferably 10% to 16%, by weight, which proportion provides antiperspirant efficacy at use concentrations.

The major component of the base is water, and this component is present in an amount of 55% to 78%, preferably 65% to 74%, by weight of the base. The water acts as a solvent for the antiperspirant agent and the solution of antiperspirant agent and water comprises the disperse phase of the base as well as the disperse phase of the aerosol antiperspirant composition. Usually, part of the formula weight of water is introduced with the antiperspirant agent which is purchosed as an aqueous solution or dispersion. The balance of the water preferably is either distilled or deionized water.

The third component of the base is an emollient-stabilizer agent which is soluble in the propellant and insoluble in water. Such agent consists of a mixture of a water-insoluble, organic liquid emollient and a water-insoluble organic liquid having a boiling point in the range of about 35° C. to 155° C., preferably 65° C. to 130° C., and most preferably 97° C. to 104° C. The weight ratio of said emollient to said liquid hydrocarbon usually ranges from 0.8:1 to 3:1 and preferably ranges from 1:1 to 2:1. Use of the mixture is essential to achieve a slightly oily deposit on the skin and satisfactory emulsion stability. Too much of the liquid emollient results in an objectionably oily or greasy deposit on the skin; whereas, too much of said liquid hydrocarbon results in reduced emulsion stability and in the skin's feeling overly wet. Thus, the emollient-stabilizer agent provides a desirable skin feel--a balance between oily and wet deposits on the skin, each of which is undesirable--and satisfactory emulsion stability in the range of 4° C. to 43° C.

The suitable emollients which are employed in the aerosol compositions of this invention may be described more specifically as water-insoluble, propellant soluble, liquid, organic compounds selected from the group consisting of $C_3$–$C_4$ esters of $C_{12}$–$C_{18}$ alkanoic acids, $C_8$–$C_{12}$ alkanols and silicone oils. Examples of satisfactory $C_3$–$C_4$ esters of $C_{12}$–$C_{18}$ alkanoic acids are isopropyl myristate, isopropyl palmitate, isopropyl iso-stearate, butyl myristate, butyl laurate and butyl iso-stearate. Examples of appropriate $C_8$–$C_{12}$ alkanols are octanol, decanol and dodecanol. Examples of acceptable silicone oils are the phenyl methyl polysiloxanes and dimethyl polysiloxanes having a viscosity of from 5 to 10000 centistrokes at room temperature and the cyclic silicones containing 3 to 6 carbon atoms. Such compounds provide a desirable film having an emollient or lubricating effect on the skin and are characterized by propellant solubility and water insolubility, which properties are important to emulsion stability. Preferred emollients are isopropyl myristate and isopropyl palmitate.

The other component of the emollient-stabilizer agent typically is a water-insoluble, propellant-soluble liquid, organic hydrocarbon derivative having a boiling point in the range of 35° to 155° C., preferably from 65° C. to 130° C. Examples of such compounds are pentane, hexane, heptane, octane, decane, methyl chloroform, methylene chloride and mixtures thereof. Preferred compounds are the $C_6$–$C_8$ hydrocarbons, with the mixtures of octanes boiling in the range of 97° C. to 104° C. being most preferred.

Such emollient-stabilizer agent constitutes the continuous phase of the water-in-oil emulsion prior to dilution with the propellant, which emulsion is referred to herein as the base. The proportion of emollient-stabilizer based upon said base is usually 10% to 25%, preferably 10% to 16%, by weight. Thus, this component constitutes a minor proportion of said base. Additionally, the weight ratio of liquid emollient to organic liquid in such emollient-stabilizer component is controlled within the range of 0.8:1 to 3:1, preferably 1:1 to 2:1, in order to control the "oiliness" of the film on the skin and to achieve the desired emulsion stability.

The final component in the base of the water-to-oil antiperspirant composition is the water-in-oil emulsifier. Such emulsifiers are $C_{12}$–$C_{18}$ alkanoic acid esters of polyhydroxylic compounds such as glycol, glycerol and sorbitol. Examples of satisfactory emulsifiers are propylene glycol stearate, glyceryl monostearate, sorbitan monolaurate, sorbitan monooleate, polyglycerol oleate sorbitan sesquioleate and mixtures of the foregoing. A preferred emulsifier is sorbitan sesquioleate. These emulsifiers manifest low solubility in water and good solubility in non-polar solvents at room temperature.

Usually, the proportion of emulsifier in the base will be in the range of 0.5% to 5%, preferably 0.75% to 4%, by weight and sufficient to provide a substantially stable water-in-oil emulsion before and after dilution with the propellant component.

As indicated above, the base comprises a mixture of anti-perspirant agent, water, emulsifier and emollient-stabilizer agent. Said base usually amounts to 50% to 75%, preferably 60% to 70%, by weight of the aerosol antiperspirant composition, with the balance thereof being the propellant. Said base is a substantially stable water-in-oil emulsion wherein the aqueous antiperspirant solution is the dispersed phase and the emollient-stabilizer agent is the continuous phase.

It is surprising that the base exists in the form of a substantially stable water-in-oil emulsion because the dispersed phase usually exceeds 80% by weight of the base. Generally, one skilled in the art would expect such proportions to yield an oil-in-water emulsion rather than a water-in-oil emulsion. The fact that a water-in-oil emulsion is achieved with such proportions facilitates preparation of the final product in the form of a substantially stable water-in-oil emulsion and also permits a maximum concentration of water in the final product. High concentrations of water are desirable in the final product because it renders the product non-flammable and reduces the cost thereof.

An optional ingredient in the inventive antiperspirant composition is a bulking or thickening agent, such as clay or a colloidal silica. Such bulking agents are finely divided particulate materials, e.g., colloidal silica may have an average particle size in the range of 0.001 to 0.03 microns. Clays which may be employed in these compositions are selected from the group of montmorillonite clays and hydrophobically treated montmorillonite clays. Examples of the montmorillonite clays are bentonite, hectorite and colloidal aluminum silicates. The preferred bulking agents are hydrophobically treated montmorillonite or hectorite clays available under the trademark "Bentone" which are prepared by reacting a clay such as bentonite or hectorite in a cation exchange system with a variety of amines. Specific examples of useful Bentone ® bulking agents are Bentone ® 27, which is a stearaluminum hectorite; Bentone ® 34 which is quaternium 18 bentonite; Bentone ® 38 which is quaternium 18 hectorite; and Bentone ® 14 which is a clay extended quaternium 18 hectorite, all of which have a particle size of below about 5 microns and are commercially available from NL Industries, Inc. A preferred clay is Bentone ® 38.

When the bulking agent is used, it is employed in amounts of from 0.1 to about 3%, preferably from 0.25 to 1.50%, by weight. The proportion of suspending agent must be controlled to avoid undesirable thickening of the product during aging at room temperature, i.e., 23° C. However, when present, the suspending agent results in a deposit on the skin which is less wet.

In addition to the foregoing components, other components optionally may be included to improve the aesthetic properties and consumer acceptability of the composition. For example, up to 1% by weight of perfume or color may be included for aesthetic purposes. Futhermore, small amounts of other components may be included for special effects or purposes. For example, up to 1% by weight of propylene carbonate may be included to facilitate dispersion of clay bulking agent when it is present. Similarly, from 0.2% to 1% by weight of a germicide or bactercide such as Irgasan DP 300 ® may be incorporated. Also, small amounts of corrosion inhibitors, such as sodium benzoate, and small amounts of antioxidants, such as 2,6 ditertiary paracresol, may be included where desired. Finally, small amounts of water-insoluble, propellant-soluble emollients or organic polymers having skin effects or vitamins or talc or propellant-soluble organic solvents may be included.

The practice of this invention utilizes standard aerosol containers of metal or glass, standard dip tubes and vapor tap valves with a mechanical break-up outlet of standard design. The valve which is sealed in the container to produce a closed system comprises a pre-mixing chamber and a secondary mixing chamber. The premixing chamber has two orifices, namely, a body orifice in cooperative engagement with a dip tube so that the emulsified liquid coming up the dip tube passes through the orifice and into the pre-mixing chamber and a vapor tap orifice communicating with the vapor phase of the system so that the propellant vapor passes into the pre-mixing chamber where it mixes with the liquid from the dip tube. The mixture thus produced passes then into the secondary mixing chamber which has two orifices, a stem orifice and an exit orifice. The stem orifice communicates with the premixing chamber so that mixed liquid and propellant vapor pass readily into it. The exit orifice communicates with the atmosphere and is constructed with a mechanical obstruction so that the mixture coming from the secondary mixing chamber is broken up into a plurality of streams. An exit orifice having a mechanical obstruction is referred to herein as a mechanical break-up outlet.

Obviously, a fair amount of latitude is possible in the valving of a container of this invention, but some generalizations may be made. The body orifice may be from 0.5 mm. to 2.5 mm. in diameter and is generally equal to or larger in size than the stem orifice which is from 0.25 mm. to 0.76 mm. in diameter and generally larger than the vapor tap orifice which is usually from 0.3 mm. to 0.65 mm. in diameter. The mechanical break-up outlet is always smaller than the body orifice. An especially useful valving system is one in which the stem orifice is 0.40 mm. in diameter, the body orifice is 1.57 mm. in diameter, the vapor tap orifice is 0.58 mm. in diameter and the mechanical break-up outlet is 0.50 mm. in diameter. This preferred valve assembly produces good results with respect to size of the droplets in the spray.

Generally, the aerosol compositions are prepared by admixing the essential components with the exception of the propellant to form a substantially stable water-in-oil emulsion which is filled into the desired container. An appropriate valve having an attached dip tube is employed to close the container. Thereafter, the propellant component under pressure is added through the valve and dip tube, and the contained and its contents are agitated to achieve the inventive aerosol antiperspirant product.

In the preparation of the base, the emollient-stabilizer is prepared by admixing the emollient liquid with the organic liquid to form a homogeneous liquid. Moderate agitation is employed forming said liquid and, preferably, such mixture is formed in a jacketed mixer so that the temperature may be controlled in the range of 10° C. to 25° C. to minimize evaporation of said organic liquid. Thereafter, the emulsifier is dissolved in said liquid mixture with moderate agitation followed by addition of bulking agent if present. Finally, the weight of this mixture is checked and, if required, any organic liquid lost by evaporation is added. Next, a mixture of the formula weight of water and the antiperspirant solution is added slowly to the resultant homogeneous liquid with vigorous agitation which is preferably supplied by a homogenizer mixer. Thereafter, perfume and any organic liquid lost be evaporation are added. A substantially stable water-in-oil emulsion results upon completion of the addition of said homogeneous liquid. Such emulsion has a viscosity of from 450 centipoises (cps.) to 3,000 cps. at 23° C. without Bentone ® 38 bulking agent and 45,000 cps. to 60,000 cps. with Bentone ® 38 bulking agent when measured using a Brookfield RVT Viscometer with a #3 spindle rotating at 10 r.p.m.

A preferred method of manufacture comprises slow addition of the formula weight of water to the resultant, homogeneous, organic liquid to form a stable water-in-oil emulsion prior to addition of the aqueous antiperspirant solution. Again, a homogenizer mixer is used for agitation and the mixing is carried out at a temperature in the range of 10° C. to 25° C. The resultant water-in-oil emulsion made by this process exhibits improved stability both before and after dilution with the liquid propellant.

The following examples will serve to illustrate the new composition invention. In the examples as well as throughout the specification all parts and percentages are by weight.

EXAMPLE 1

A satisfactory aerosol antiperspirant product having the following composition is formulated and packaged in an aerosol container under pressure.

|  | Percent |
|---|---|
| Part A |  |
| Isopropyl myristate | 7 |
| $C_8$ hydrocarbon mixture[a] | 5 |
| Perfume | 1.0 |
| Sorbitan sesquioleate | 0.83 |
| Hydrophobic montmorillonite clay[b] | 1.0 |
| Part B |  |
| 20% aluminum chlorohydroxide solution | 64 |
| Distilled water | 20.17 |
|  | 100.00 |
| Base (Mixture of Parts A and B) | 70 |
| Hydrocarbon propellant (80% isobutane and 20% propane) | 30 |
|  | 100.0 |

[a]Mixture of $C_8$ isoparaffins boiling in the range of 97° C.–104° C. containing about 0.2% non-volatiles and obtained under the name Isopar C.
[b]Purchased from N. L. Industries under the name Bentone 38 (Trademark)

Part A of the foregoing product is prepared by admixing the isopropyl myristate, $C_8$ hydrocarbons and perfume to form a singlephase liquid. The sorbitan sesquioleate emulsifier then is mixed with the organic liquids. Next, the clay is dispersed in the organic liquid mixture with good agitation. Thereafter, Part B comprising the aqueous solution of aluminum chlorohydroxide is slowly added to Part A with vigorous agitation to form a stable water-in-oil emulsion. Finally, the oil-in-water emulsion is charged into an aerosol container closed with a valve and the propellant is added through the dip tube. The container is then shaken.

When the product is dispensed from the container by actuating the vapor tap valve (body orifice of 1.57 mm. stem orifice of 0.40 mm. and vapor tap orifice of 0.58 mm.), the product sprayed at a rate of 0.45–0.5 gm./sec. when using a two-piece actuator with a terminal orifice of 0.50 mm. diameter.

When the containers of the product were tested for flammability using the standard flame extension test, the product showed no flame extension and no flash back. (Flame extension test is outlined in the 1980 edition of Standard Test Methods published by the British Aerosol Manufacturers Association.) In fact, the flame was extinguished each time a single container was tested.

This product was compared with a conventional aerosol product of the anhydrous type wherein a particulate astringent salt is suspended in a liquid vehicle comprising a major proportion of chlorofluorohydrocarbon propellant. The composition of this example was observed to produce a warmer spray, and this observation was statistically significant at the 98% confidence level. Additionally, the panelists observed that the exemplified composition was wetter on the skin and that both products were effective antiperspirants.

The product was found to be stable after aging for six months at 4° C., 23° C. and 43° C. Futhermore, the product was stable after being subjected to three freezing and thawing cycles.

EXAMPLE 2

A preferred antiperspirant product of the following composition is prepared according to the method of Example 1.

|  | Percent |
|---|---|
| Part A |  |
| Isopropyl myristate | 7.5 |
| $C_8$ hydrocarbon mixture | 5.0 |
| Perfume | 0.6 |
| Sorbitan sesquioleate | 0.75 |
| Part B |  |
| 20% aluminum chlorohydroxide | 75.0 |
| Distilled water | 11.15 |
|  | 100.00 |
| Base (Mixture of Parts A and B) | 60 |
| Hydrocarbon propellant (80% isobutane and | 40 |

-continued

| | Percent |
|---|---|
| 20% propane) | |

The foregoing product is a substantially stable water-in-oil emulsion. Samples of such product have aged for more than one year at room temperature in both lacquered aluminum and tinplate containers without any visible corrosion. Such result further confirms the stability of the water-in-oil emulsion because if the water were in the continuous phase or in a separated phase, can corrosion would be expected.

When the composition of Example 2 is prepared by first admixing Part A with the distilled water portion of Part B with good agitation and thereafter adding the aqueous aluminum chloride portion of Part B, a water-in-oil emulsion of improved stability is obtained.

EXAMPLE 3

The composition of Example 1 is repeated with the exception that a mixture of chlorofluoro-hydrocarbon propellants (Propellant 12/114 50:50) is substituted for the $C_3$–$C_4$ hydrocarbon propellant and a satisfactory antiperspirant product in the form of a water-in-oil emulsion is achieved.

Other antiperspirant compositions falling within the scope of this invention are set forth in Examples 4–9 below. Each composition is made according to the method described in Example 1.

EXAMPLE 4

| | Percent |
|---|---|
| Part A | |
| Isopropyl myristate | 5 |
| Pentane | 8 |
| Sorbitan sesquioleate | 4 |
| Part B | |
| 20% aluminum chlorohydroxide | 75 |
| Distilled water | 8 |
| | 100.0 |
| Base (Part A and Part B) | 62 |
| Propellant (80% isobutane and 20% propane) | 38 |
| | 100.0 |

EXAMPLE 5

| | Percent |
|---|---|
| Part A | |
| Isopropyl myristate | 5 |
| Pentane | 8 |
| Sorbitan sesquioleate | 2 |
| Part B | |
| 20% aluminum chlorohydroxide | 75 |
| Distilled water | 10 |
| | 100.0 |
| Base (Part A and Part B) | 62 |
| Propellant (80% isobutane and 20% propane) | 38 |
| | 100.0 |

EXAMPLE 6

| | Percent |
|---|---|
| Part A | |
| Isopropyl myristate | 5 |

| | Percent |
|---|---|
| Pentane | 13 |
| Sorbitan sesquioleate | 4 |
| Part B | |
| 20% Aluminum chlorohydroxide | 65 |
| Distilled water | 13 |
| | 100.0 |
| Base (Part A and Part B) | 70 |
| Propellant (80% isobutane and 20% propane) | 30 |
| | 100.0 |

EXAMPLE 7

| | Percent |
|---|---|
| Part A | |
| Isopropyl myristate | 8 |
| Pentane | 5 |
| Sorbitan sesquioleate | 1.5 |
| Part B | |
| 20% Aluminum chlorohydroxide | 65 |
| Distilled water | 20.5 |
| | 100.0 |
| Base | 70 |
| Propellant (80% isobutane and 20% propane) | 30 |
| | 100.0 |

EXAMPLES 8–9

| | Percent | |
|---|---|---|
| | 8 | 9 |
| Part A | | |
| Isopropyl myristate | 8 | 8 |
| n-Pentane | 5 | |
| $C_8$ hydrocarbon mixture | | 5 |
| Sorbitan sesquioleate | 0.75 | 0.75 |
| Part B | | |
| 20% aluminum chlorohydroxide | 65 | 65 |
| Distilled water | 21.25 | 21.25 |
| | 100.00 | 100.00 |
| Base Part A and Part B | 70 | 70 |
| Propellant (80% isobutane and 20% propane) | 30 | 30 |
| | 100.00 | 100.00 |

When the isopropyl myristate is replaced in Examples 8 and 9 with isopropyl isostearate, water-in-oil antiperspirant compositions of similar stability and effectiveness result. On the other hand, an unstable product resulted when diisopropyl adipate was substituted for isopropyl myristate in the composition of Example 9.

Additionally, use of an aluminum chlorohydroxide-propylene glycol complex (Rehydrol ASC) as the antiperspirant salt in the composition of Example 9 yields a satisfactory product.

The invention has been described with respect to various examples and illustrations thereof but is not to be limited to these because it is clear that one of skill in the art, with the present description before him, will be able to utilize substitutes and equivalents without departing from the invention.

We claim:

1. An aerosol antiperspirant composition in the form of a substantially stable water-in-oil emulsion which does not result in reversion of said emusion when it is sprayed from a container consisting of 25% to 50% by weight of a liquefied, normally gaseous propellant and 50% to 75% of a base consisting essentially of, by weight:

A. 4% to 20% of at least one water-soluble, astringent salt having antiperspirant efficacy;

B. 0.5% to 5% of a water-in-oil emulsifier;

C. 10% to 25% of a propellant-soluble emollient-stabilizer agent consisting of (1) a water-insoluble, organic, liquid emollient selected from the group consisting of isopropyl esters of $C_{12}$–$C_{18}$ alkanoic acids, $C_8$–$C_{12}$ alkanols and silicone oils and (2) a water-insoluble organic liquid hydrocarbon having a boiling point in the range of 65° C. to 130° C., the weight ratio of (1) to (2) being in the range of 0.8:1 to 3:1; and D. 55% to 78% of water, said base being in the form of a substantially stable water-in-oil emulsion.

2. A composition according to claim 1 wherein said organic liquid is a hydrocarbon having a boiling point in the range of 97° C. to 104° C.

3. A composition according to claim 2 wherein said emollient is an isopropyl ester of a $C_{12}$–$C_{16}$ alkanoic acid and the weight ratio of said emollient to said organic liquid is in the range of 1:1 to 2:1 with the concentration of said emollient-stabilizer agent being from 12% to 18% by weight.

4. A composition according to claim 3 wherein said astringent salt is an aluminum compound.

5. A composition according to claim 4 wherein said aluminum compound is basic aluminum chloride.

6. A composition according to claim 3 wherein said emulsifier is sorbitan sesquioleate.

7. A composition according to claim 1 wherein said liquefied, normally gaseous propellant is a $C_3$–$C_4$ hydrocarbon.

8. A composition according to claim 1 which consists of 30% to 40% by weight of a $C_3$–$C_4$ hydrocarbon propellant and 60% to 70% by weight of a base consisting essentially of by weight:

A. 10% to 16% of basic aluminum chloride;

B. 0.75% to 4% of sorbitan sesquioleate;

C. 12% to 18% of a mixture of (1) an isopropyl ester of a $C_{12}$–$C_{18}$ alkanoic acid and (2) a liquid hydrocarbon having a boiling point in the range of 97° C. to 104° C. with the weight ratio of (1) to (2) being in the range of 2:1 to 1:1; and D 65% to 74% of water.

9. A process of making an article of manufacture consisting of a valved container containing a water-in-oil emulsion which does not result in reversion of said emulsion when it is sprayed from a container which comprises the steps of:

A. Forming a liquid mixture at a temperature of from 10° C. to 40° C. of 12 to 18 parts by weight of an isopropyl ester of a $C_{12}$–$C_{18}$ alkanoic acid and a liquid hydrocarbon having a boiling point in the range of 65° C. to 130° C. with the weight ratio of said ester of said hydrocarbon being from 2:1 to 1:1;

B. Dissolving an oil-in-water emulsifier in the liquid mixture of Step A with agitation;

C. Adding to the mixture of Step B, 8 to 22 parts by weight of water with vigorous agitation to form a water-in-oil emulsion D. Adding from 50 to 80 parts by weight of an aqueous solution of aluminum chlorohydroxide to the water-in-oil emulsion of Step C with strong agitation;

E. Filling 60 to 70 parts by weight of the water-in-oil emulsion of Step D into an aerosol container and closing said container with a vapor tap valve; and F. Adding 30 to 40 parts by weight of a $C_3$–$C_4$ hydrocarbon propellant under pressure to said aerosol container through the valve thereof and agitating the contents whereby a substantially stable aerosol antiperspirant composition is formed.

* * * * *